United States Patent [19]
Vroemen et al.

[11] Patent Number: 5,897,995
[45] Date of Patent: Apr. 27, 1999

[54] ENZYMATIC PRODUCTION OF GLUCONIC ACID OR ITS SALTS

[75] Inventors: Albert J. Vroemen, Marq En Baroel; Marc Bévérini, Lille, both of France

[73] Assignee: Gist-brocades, B.V., Netherlands

[21] Appl. No.: 08/765,663

[22] PCT Filed: May 13, 1996

[86] PCT No.: PCT/EP96/02128

§ 371 Date: Apr. 16, 1997

§ 102(e) Date: Apr. 16, 1997

[87] PCT Pub. No.: WO95/33631

PCT Pub. Date: Dec. 14, 1995

[30] Foreign Application Priority Data

May 12, 1995 [EP] European Pat. Off. .............. 95201247

[51] Int. Cl.⁶ ................... C12P 7/64; C12P 7/58; C12N 9/96; C12N 9/04
[52] U.S. Cl. .............. 435/137; 435/14; 435/27; 435/134; 435/190
[58] Field of Search ................ 435/134, 137, 435/27, 14, 190

[56] References Cited

U.S. PATENT DOCUMENTS

| | | |
|---|---|---|
| 3,619,396 | 11/1971 | Walon . |
| 3,935,071 | 1/1976 | Bergmeyer et al. . |
| 4,418,147 | 11/1983 | Muetgeert et al. . |
| 4,460,686 | 7/1984 | Hartmeier . |
| 5,292,773 | 3/1994 | Hirsch et al. . |

FOREIGN PATENT DOCUMENTS

| | | |
|---|---|---|
| 0 017 708 B1 | 2/1980 | European Pat. Off. . |
| 0 114 630 A2 | 1/1984 | European Pat. Off. . |
| 1590031 | 10/1968 | France . |
| 2029645 | 1/1970 | France . |
| 2177931 | 3/1973 | France . |
| 2 441 658 | 11/1979 | France . |
| 92739 | 10/1987 | Romania . |
| 1 249 347 | 10/1971 | United Kingdom . |
| 2 106 521 | 9/1982 | United Kingdom . |
| WO 91/17235 | 11/1991 | WIPO . |

OTHER PUBLICATIONS

Hartmeier et al "Biotech Lett" 5 pp. 743–748 (1983).
Doppner et. al "Starch" 36 pp. 283–287 (1984).
Constantinescu et al "Rev. de Chimie" 41 5–6 pp. 496–502 (1990).
Rosenberg, M., et al., "Gluconic acid production by *Aspergillus niger* with oxygen supply by hydrogen peroxide," *Bioprocess Engineering* (1992) 7:309–313.
Hartmeier, W., et al., "Preparation and Properties of Mycelium Bound Glucose Oxidase Co–Immobilized with Excess Catalase," *Biotechnology Letters* (1983) 5(11):743–748.
Liu, Wen–Hsiung, et al., "Enzymatic Oxidation of Glucose via Crab Chitin Immobilized Glucose Oxidase and Catalase," *Proc Natl Sci Counc ROC* (1980) 4(3):338–344.
"The Influence of Peroxide–Stabilizing Agents on Enzyme Deactivation by $H_2O_2$," in *Biotechnology and Bioengineering* (1977) 19:157.
Döppner, T., et al., "Glucose Oxidation by Modified Mould Mycelium," *starch/stärke* (1984) 36(8):283–287.

*Primary Examiner*—Herbert J. Lilling
*Attorney, Agent, or Firm*—Morrison & Foerster LLP

[57] ABSTRACT

An enzymatic process for the conversion of glucose into gluconic acid, uses concentrated glucose solutions. The process employs a combination of glucose oxidase and catalase enzymes which may be obtained from an *Aspergilltus niger* strain and has a high ratio of catalase:glucose oxidase activity. The enzymatic process requires less time than conventional fermentation processes, the yield of the conversion is close to 100% and the obtained gluconic acid/gluconate solutions do not contain impurities.

16 Claims, No Drawings

ENZYMATIC PRODUCTION OF GLUCONIC ACID OR ITS SALTS

FIELD OF THE INVENTION

The present invention relates to the enzymatic production of gluconic acid. More specifically, the invention provides a method for the conversion of glucose into gluconic acid using the enzymes glucose oxidase and catalase.

BACKGROUND OF THE INVENTION

Gluconic acid is a mild acid with many applications which comprise: its technical use as a complexing agent in industrial cleaning of metal surfaces; its use in the textile industry, in detergents and in concrete; as a food additive in beverages and also in bread and feed; and in pharmaceutical preparations as a chelating agent for ions like Fe. The gluconic acid used in food applications and especially in pharmaceutical preparations must be very pure.

Up until now the production of gluconic acid at industrial scale has been carried out using a fermentation process. Selected microorganisms such as e.g. Aspergillus or Gluconobacter species are grown in a fermenter which is at least equipped with air supply, pH control and temperature control. Optimal conditions are chosen for good growth of the microorganism and optimal development of the enzyme complex capable of converting glucose into gluconic acid/gluconate. At the end of the growth phase, a glucose solution is added to the fermentation broth and aeration is continued. The glucose is converted by the enzymatic complex into gluconic acid. Usually the pH is controlled by the addition of alkali, in which case the majority of gluconic acid will be present as a gluconate salt.

In fungi, glucose is transformed into gluconic acid by an enzymatic complex consisting of glucose oxidase (Gox) and catalase. Glucose oxidase catalyses the reaction:

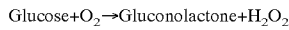
$$Glucose + O_2 \rightarrow Gluconolactone + H_2O_2$$

The hydrogen peroxide is subsequently split by catalase:

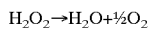
$$H_2O_2 \rightarrow H_2O + \tfrac{1}{2}O_2$$

The conversion of gluconolactone into gluconic acid can be catalysed by the enzyme gluconolactonase but can also occur spontaneously:

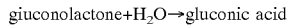
$$gluconolactone + H_2O \rightarrow gluconic\ acid$$

Thus, the following overall reaction results:

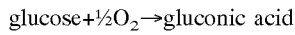
$$glucose + \tfrac{1}{2}O_2 \rightarrow gluconic\ acid$$

The enzymatic complex glucose oxidase/catalase is present in several micro-organisms belonging e.g. to the classes Aspergillus and Penicillium. Also bacteria like Acetobacter and Gluconobacter are capable of converting glucose into gluconic acid but the bacteria use a different mechanism: *Gluconobacter oxydans* contains two types of glucose dehydrogenases which convert glucose into gluconolactone without the formation of hydrogen peroxide. At this moment, industrial processes for the production of gluconic acid use almost exclusively selected strains of *Aspergillus niger* or *Gluconobacter oxydans* in a fermentation process.

The enzymes glucose oxidase and catalase are rather well characterized. The glucose oxidase of *A.niger* is a glycoprotein with a molecular weight of about 150 kDa and contains prosthetic groups of FAD; the enzyme is active between pH 4 and 7 with an optimal activity at pH 5,5; the enzyme is optimally active at temperatures between 20° and 40° C.; the isoelectric point is about 4,2; the $K_m$ for glucose is 0,11M at 27° C. and the $K_m$ for oxygen is 0.48 mM. The catalase of *A.niger* has a molecular weight of 250 kDa; the enzyme is active between pH 2 and 7; the optimal temperature is 25° C.; the isoelectric point is about 5,4; the $K_m$ for hydrogen peroxide is about 1,1M or about 37 g/l. The latter means that the affinity of the enzyme catalase for its substrate is very poor.

Taking into account the applications of gluconic acid, the existing fermentative production processes have the following drawbacks. Complex production media are used which, besides glucose, must contain all kinds of nutrients for the growth of the microorganisms, which are costly and give impurities. At the end of the bioconversion the broth contains many byproducts formed during the fermentation such as coloured substances and organic acids other than gluconic acid, such as e.g. citric acid, oxalic acid and 5-keto-gluconic acid. The overall production time includes both the growth time and the bioconversion time and usually requires several days. With fungi, the yield based on glucose is significantly lower than the theoretical maximum yield of 100% because part of the glucose added is used by the microorganism for growth, i.e. for biomass production in stead of gluconic acid production; with Gluconobacter, the yield can be close to 100% but this organisms needs expensive nutrients for growth (W. Olijve, thesis University of Groningen, 1978). Both with fungi and bacteria, at the end of the bioconversion the biomass contained in the broth must be removed. Moreover, especially for the food and pharmaceutical preparations the gluconic acid must undergo extensive further purification in order to remove the above mentioned nutrients and byproducts, which often requires multiple purification steps.

In view of these drawbacks of the fermentative gluconic acid production process, numerous attempts have been made to develop an enzymatic process using the enzymes glucose oxidase and catalase. However, at present no economically feasible enzymatic process for the production of gluconic acid is available. The major reason for this is the low stability of the enzymes involved, even when immobilized. The instability of the enzymes is in fact mainly caused by one of the reaction products, i.e. hydrogen peroxide, which at higher concentrations rapidly inactivates both glucose oxidase and catalase.

The following disclosures exemplify the state of the art of the conversion of glucose into gluconic acid for both fermentation and enzymatic processes:

FR-A-1 590 031 describes a fermentation process for the conversion of glucose in to gluconic acid comprising the stepwise addition of glucose to the fermentation broth. Even though FR-A-1 590 031 suggests that isolated enzymes could also be applied in this process, however, it is not disclosed that this can be done using high glucose concentrations while achieving a conversion rate of more than 50%.

Rosenberg et al. (1992, Bioprocess Eng. 7: 309–313) describe a fermentation process for gluconic acid production in which an a high catalase containing *A.niger* mutant is used and wherein hydrogen peroxide is applied as oxygen donor. However, as already mentioned, hydrogen peroxide inactivates glucose oxidase and cataiase in isolated form.

Liu et al. (1980, Proc. Natl. Sci. Counc. Repub. China 4: 338–344) use an immobilized enzyme system comprising glucose oxidase and catalase from the fungus *Pullularia pullulans* to convert glucose solutions of no more than 10% (w/v).

FR-A-2 177 931 discloses an enzyme-system in which catalase and glucose oxidase are immobilized in close proximity of each other in order to protect glucose oxidase from rapid inactivation by hydrogen peroxide. FR-A-2 177 931 teaches to immobilize the enzymes in a catalase/glucose oxidase-activity ratio of at least 1, preferably up to 200. This enzyme system is, however, only used to convert glucose solutions of no more than 5.5% glucose (w/v).

Hartmeier and Döppner (1983, Biotechnol. Lett. 5: 743–748; see also: Döppner and Hartmeier, 1984, Starch 36: 283–287) use the permeabilized mycelium of a glucose oxidase and catalase producing *A.niger* strain which is coimmobilized with additional catalase to convert glucose into gluconic acid. In this coimmobilized enzyme system catalase and glucose oxidase are present in activity ratios of up to 7600 Baker Units of catalase over 2000 Sarett Units of glucose oxidase (in International catalase Units this corresponds to about a ratio of about 3950). However, all conversions are carried out with glucose solutions of no more concentrated than 10% (w/v).

RO-92739 describes a process for preparing gluconic acid from glucose in a cyclic process using soluble catalase and glucose oxidase. The glucose concentration used in all examples is 10% (w/v). Catalase/glucose oxidase ratios of up to 200 are used to reach conversion rates of up to 98%.

In a similar cyclic process, Constantinescu et al. (1990, Rev. de Chimie, 41, 5–6: 496–502) test glucose concentrations ranging from 3–20 (w/v). A glucose concentration of 10% (w/v) provides optimal conditions resulting in a conversion rate of 93%. However, when using 15% (w/v) glucose the conversion rate is only about 40%.

FR-A-2 029 645 is concerned with an enzymatic process for the production of gluconic acid in which electrodialysis is used to separate glucose oxidase and the gluconic acid produced and in which hydrogen peroxide is used as oxygen donor. Subsequently fresh glucose is added to restart the reaction. This process is repeated several times. However, a dextrose equivalent of only 100 is used and the yield of gluconic acid is less than 50%.

EP-A-0 017 708 discloses an enzymatic process in which catalase and glucose oxidase are immobilized in a ratio of at least 1:6 in Baker Units of catalase activity and Sarett Units of glucose oxidase activity. The immobilized enzymes are used to convert glucose solutions of 10% and 20% extremely low temperatures: 2° C. and 8° C., respectively. Such low temperatures are, however, not economically feasible at large industrial scale because it would require immense cooling capacity in view of the exothermic nature of the reaction.

Hence, thus far one has either used low glucose concentrations or used low temperatures. Serious drawbacks of the use of low glucose concentrations are, however, that the output (productivity per volume) of the equipment used is low and that diluted gluconic acid solutions are obtained which require energy-intensive removal of the excess water.

There is therefore a need for an enzymatic process for the conversion of glucose into gluconic acid in which high glucose concentrations, i.e. higher than 10% (w/v), can be used, while obtaining a conversion of more than 50% of the glucose used and which can be performed at a temperature of more than 10° C.

SUMMARY OF THE INVENTION

The present invention provides a process for the enzymatic conversion of glucose into gluconic acid, in which a glucose solution having a concentration of at least 10% (w/v) is converted into gluconic acid at good yield, viz. 50% or more, in the presence of glucose oxidase and catalase using an excess of activity units of catalase relative to oxidase and whereby the conversion takes place at a temperature of more than 10° C.

DESCRIPTION OF THE INVENTION

The present invention for the first time discloses an enzymatic process for the conversion of glucose into gluconic acid, in which a glucose solution having a concentration of at least 10% (w/v) is converted into gluconic acid in a yield of at least 50% in the presence of glucose oxidase and catalase using an excess of activity units of catalase relative to oxidase and whereby the conversion takes place at a temperature of more than 10° C.

Surprisingly we have found that it is possible to obtain complete conversion of glucose into gluconic acid using a glucose concentration well in excess of 10% (w/v) when an enzyme preparation is used which has a catalase/glucose oxidase activity ratio in International over Sarett Units which is in excess of 140, or even well above 400. Liquid or spray dried enzyme preparations were mixed with glucose solutions with a glucose concentration ranging from 27.3% to 54.5% (w/v) which were buffered at pH 6.0. The conversion was carried out in a standard laboratory fermenter equipped with air supply, pH and temperature control. Enzymatic conversion above 99% of glucose into gluconic acid was achieved in 9 to 33 hours, depending on the reaction conditions used.

The temperature at which the conversion is performed will be higher than 10° C., preferably higher than 15° C. and more preferably 17° C. of higher, still more preferable 20° C. or higher and most preferably 25° C. or higher. The upper temperature limit of the conversion will depend on the thermostability of the enzymes involved, in case the enzymes are obtainable from the fungus *Aspergillus niger* the temperature of the conversion should preferably be less than 40° C.

A process for the enzymatic conversion of glucose into gluconic acid is herein defined to exclude any such process which is fermentative and uses intact viable cell which are capable of growth. The enzymatic process uses enzymes in isolated form or in crude preparations, or mixtures thereof; the enzymes can be used in soluble form and/or can be immobilized; an enzymatic process may even include the use of permeabilized and/or immobilized cells, optionally mixed with additional enzymes, as long as these cells are no longer viable or capable of growth.

The use of a glucose concentration higher than 10% (w/v) in the enzymatic process is not only intended to mean that the reaction is initiated with a glucose concentration higher than 10% (w/v) or that the reaction is started at a lower concentration and that glucose is added such that at least at some point in time during the conversion reaction the actual glucose concentration is in excess of 10% (w/v), but is rather defined as that at some point during the reaction the sum of the glucose concentration and the gluconic acid/gluconates concentration on a molar bases is higher than 0.05556M, which would correspond to 10% (w/v) glucose if only glucose is present. Also included is the feeding of a glucose solution with a concentration of glucose in excess of 10% (w/v) during the conversion reaction.

The glucose concentrations are herein defined as percentage weight per volume (w/v), i.e. a glucose concentration of 10% means 100 g glucose/liter, unless indicated otherwise. The skilled person will understand that the terms gluconic acid and gluconate are used interchangeably. Complete conversion is herein understood to mean that the residual glucose is less than 1% of the original value or the conversion is more than 99%.

In a preferred embodiment a combination of the enzymes glucose oxidase and catalase is used for the conversion of glucose into gluconic acid. Preferably at least one of these enzymes is obtained from a fungus in which case the fungus is preferably an Aspergillus or a Penicillium species. In a more preferred embodiment the enzyme(s) are obtained from a strain belonging to the *Aspergillus niger* group as defined by Raper and Fennell (1965; "The genus Aspergillus", The Williams and Wilkinson Company, Baltimore), in which case the *A.niger* is most preferred. The enzymes to be used for the conversion of glucose into gluconic acid can be all obtained from a single strain or, alternatively, can be separately obtained from different strains, and subsequently mixed to obtain the desired mixture of the enzymes involved. The production strains used for the production of the enzyme preparations of the invention can be wild type strains or, alternatively, strains modified by classical mutagenesis and/or by the use recombinant DNA technology. The modifications may comprise modification of the regulation of the production rate and/or production levels of the enzymes, a reduction of the level of unwanted side-activities in the enzyme preparations obtained and/or may include modification of the properties of the enzymes themselves through the use of chemical modification and/or protein engineering. Particularly advantageous are modifications which result in improved stability and/or oxidation-resistance of the enzymes to be used in the process of the invention.

The enzyme preparation of the invention comprises catalase and glucose oxidase and is able to convert glucose in a yield of at least 50% in an aqueous medium containing at least 25% (w/v) glucose. Preferably the enzymes catalase and glucose oxidase are present in an activity ratio in excess of 200 IU/SU, respectively, wherein IU is defined as the International catalase Unit and SU is defined as the Sarett glucose oxidase Unit (see Experimental). More preferably, the activity ratio of the enzyme preparation of the invention is higher than 400 IU/SU. Even more preferable is an activity ratio in excess of 700 IU/SU.

The enzyme preparations of the invention are preferably applied as soluble enzymes but may also be applied as immobilized enzymes. However the use of immobilized enzymes is more expensive and complicates oxygen supply. Many different methods for the immobilization of glucose oxidase and/or catalase are known in the art as most work on the enzymatic conversion of glucose into gluconic acid has been performed using immobilized enzyme preparations.

The enzymatic process for the conversion of glucose into gluconic acid uses a glucose concentration of 10% (w/v) or higher. Preferably the glucose concentration used is higher than 15% (w/v). More preferably, a glucose concentration of 20% or higher is used. Still more preferably, a glucose concentration of 30% or higher is used. Even a saturated glucose solution can be used, however, this may cause problems with the oxygen transfer. Also crude glucose solutions can be used which are obtained in existing saccharification processes (e.g. DE95 solutions), or the soluble fraction obtained after crystallization of dextrose could be used as source of glucose. Alternatively, the saccharification of polysaccharides such as starch can be combined with the conversion into a single process step or both steps can at least be performed in one and the same reactor. In these cases the enzymatic complex consisting of glucose oxidase and catalase may be supplemented with enzymes capable of the conversion of non-glucose compounds into glucose. Examples of such enzymes are e.g. carbohydrases, such as amylases, glucoamylases, pullanases or transglucosidases, and (acid) phosphatases. In the process of the invention at least 50% by weight of the glucose is converted into gluconic acid. Preferably at least 60% of the glucose is converted, more preferably at least 85% is converted and in the most preferred embodiment complete conversion occurs, which means that at least 99% of the glucose is converted.

Although in the specific embodiments of the invention, batch processes for the conversion of glucose into gluconic acid are used, in a further embodiment a fed-batch process is used in which a glucose solution is fed to the reaction mixture in which the conversion takes place. Preferably the glucose feed uses a concentrated glucose solution, i.e. higher than 10% (w/v), in order to obtain solutions with a higher concentration of gluconic acid. In still a further embodiment of the invention the erzyme preparation is also fed to the reaction mixture. Preferably a separate feed is used for the enzyme solution such that it can be controlled independent from any other parameter. It will be understood that the process of the invention is preferably used at industrial scale, i.e. using a reactor (e.g. a fermenter) with a working volume in excess of 1 $m^3$, more preferably a working volume in excess of 10 $m^3$, or most preferably a working volume in excess of 25 $m^3$. In order to be able to control the enzymatic process, the reactor is preferably equipped with at least air supply, a stirring device, pH control, temperature control. More preferably, the reactor is also endowed with measurement of the dissolved oxygen concentration, the amount of air given, and the amount of oxygen in the outlet air. In this case, the oxygen consumption (which is proportional to the amount of gluconic acid produced) can be measured "on line". Preferably air is used as source of oxygen in the reaction of the present invention. However, in an alternative embodiment of the invention, enriched air, oxygen and/or even hydrogen peroxide are used as (additional) source of oxygen.

One advantage of the process of the invention is that it can be performed in the type of fermenters which are used for the fermentative production of gluconic acid, allowing a switch from the fermentative to the enzymatic process without substantial investments.

The preferred conditions under which the process of the invention is performed are those which are optimal for the enzymes used. In case the enzymes glucose oxidase and catalase are obtained from *A.niger*, the preferred conditions are as follows:

The pH is preferably in the range between pH 4.0 and pH 7.0, more preferably between pH 5.0 and pH 6.5, most preferably the pH is set between pH 5.5 and 6.0.

The temperature is preferably in the range between 15 and 40° C., more preferably between 17 and 30° C. and most preferably between 20 and 25° C.

The ratio of the activities of the enzymes catalase and glucose oxidase used in the process of the invention is higher than 2.0 IU/SU. Preferably the activity ratio is higher than 55, more preferably an activity ratio in excess of 140 IU/SU is used, still more preferably the activity ratio exceeds 200 IU/SU and in the most preferred embodiment, the activity ratio is 417 IU/SU or higher.

If the stirring conditions in the reactor are good, in principle the use of a buffer is not required. However, to improve the control of the pH, a buffer can be added to the reaction mixture. Although in the specific embodiments of the invention a phosphate buffer is used, a more preferred buffer system uses gluconic acid and gluconate to set the pH. In case the latter buffer system is used, no extra costs are involved and the final product will not be contaminated with buffer components. During the conversion alkali solutions, preferably concentrated alkali solutions, can be added to neutralize the gluconic acid produced. The amount of alkali consumed at constant pH provides an direct indication of the amount of gluconic acid produced. When the production of a specific gluconate salt is desired, the compound used to adjust the pH can be chosen accordingly, e.g. $CaCO_3$ will produce Ca-gluconate and NaOH will produce Na-gluconate.

In a further embodiment of the invention protective agents are added to the enzymatic reaction in order to improve the performance of the enzymes involved. In particular the protective agents should improve the stability and/or protect the enzymes involved against oxidation. Examples of such protective agents include proteinaceous material, casein, methionine, quinine, or other compounds which can be oxidated by hydrogen peroxide. Preferably the protective agents and/or the oxidated derivatives thereof, are not toxic and/or can be easily removed from the final product, i.e. the gluconic acid solution. We have also found that the inclusion of 50 mM mannitol exerts a positive effect on the stability of the enzymes. The invention thus includes the addition of polyol compounds such as mannitol, sorbitol and glycerol.

The enzymatic process of the invention offers inter alia the following advantages:

In essence, only glucose is present as a medium component. If necessary, small quantities of buffer are added to improve control the pH. In principle, a gluconate/gluconic acid buffer system can be used, in which case the only impurity is the enzyme solution itself of which the quantity is very small;

no biomass is produced during the conversion and because of this, the solution remains clear;

by-products are minimized;

yield based on glucose can in principle be close to 100%;

the production time consists only of the time necessary for the conversion and is, therefore, significantly shorter than the time a fermentation process which requires a growth phase;

in principle, any concentrated glucose solutions can be used, including impure glucose solutions. The use of the latter may result in the need for additional purification. In a glucose factory, the concentration of glucose in the syrup after the saccharification steps is between 30 and 40% w/w. Sometimes, these syrups are further concentrated. These solutions can be used directly for the conversion of glucose into gluconic acid in the process of the invention;

the use of concentrated glucose solutions will result in the production of concentrated gluconic acid solution which do not, or to a lesser extend, require further energy-intensive concentration;

the recovery, especially for the products which need a high purity, will be much more simple for the products obtained from the enzymatic process of the invention as compared to the products obtained from the fermentative process.

The following examples illustrate the invention.

EXPERIMENTAL

Catalase Assay in International Units

The decomposition of hydrogen peroxide ($H_2O_2$) by catalase is followed directly by the decrease in absorbance at 240 nm ($\in$240 nm=38.03 in the experimental conditions). This method was adapted from H. U. Bergmeyer et al. (1983) in: Methods of enzymatic analysis, (Bergmeyer, H. U. eds.) 3rd edition, pp. 165–166.

Definition of the International Unit:

One International Catalase Unit (referred to as IU herein) is the enzyme activity which decomposes 1 $\mu$Mole $H_2O_2$ per minute in 5 ml Phosphate buffer (0.01M—pH 6.8) from an initial $H_2O_2$ concentration of 2 mmole.

The activity is then expressed in units per gram or ml of enzymatic solution.

Description of the Method:

To 5 ml substrate solution ($H_2O_2$ 0.45M in 0.01M Phosphate buffer pH 6.8) is added 1 ml enzyme solution.

After 5 minutes of incubation time at 25° C., the reaction is stopped by addition of 2 ml of 1M sulphuric acid. The mixture is then 20 times diluted before absorbance measurement at 240 nm against a blank without enzyme solution.

The amount of decomposed $H_2O_2$ is then calculated in reference to the initial absorbance of the substrate solution correctly diluted in the same volume mixture (containing 2 ml Sulphuric acid and 1 ml buffer instead of enzyme solution).

Glucose Oxidase Assay in Sarett Unit

Glucose oxidase oxidizes glucose to gluconic acid and hydrogen peroxide. This latter is reduced to water by peroxidase in presence of a chromogen (hydrogen donor). The optical density of the oxidized chromogen, which becomes violet in acid medium, is a measure for the glucose oxidase activity. This method was adapted from H. U. Bergmeyer et al. (1983) in: Methods of enzymatic analysis, (Bergmeyer, H. U. eds.) 3rd edition, pp. 201–202.

Definition of the Sarett Unit:

One Sarett Unit is the quantity of enzyme causing in a Warburg manometer 10 $mm^3$/minute of oxygen consumption at 30° C. by a 3.3% glucose solution in phosphate buffer pH 5.9 and with an excess of oxygen and catalase.

Description of the method:

The substrate solution prepared in phtalate buffer 0.1M pH 5.4 contains:

99 volumes of: glucose 2%+Peroxidase 1 volume of : o-dianisidine HCl (132 mg/10 ml)

The reaction medium contains:

4 ml of the substrate solution 1 ml of enzyme solution

It is then incubated at 37° C. for 10 minutes. The reaction is stopped by addition of Sulphuric acid 10M (5 ml) and the absorbance of the solution is read at 540 nm.

The activity measurement according to this calorimetric method is then expressed in Sarett units in reference to a calibration plot using glucose oxidase standard solutions at known Sarett units versus the corresponding calorimetric values.

Gluconic Acid Determination

The gluconic acid dosage was performed by using the D-gluconic acid test combination from Boehringer Mannheim (Cat. N° 428–191).

In the presence of gluconate Kinase, D-gluconic acid is phosphorylated by ATP to gluconate 6-Phosphate.

In the reaction catalysed by 6-phosphogluconate dehydrogenase, gluconates 6-phosphate is oxidized by NADP to ribulose-5-phosphate with the formation of NADPH. The amount of NADPH is stoichiometric with the amount of gluconic acid. The increase in NADPH is determined by means of its absorbance at 340 nm.

Glucose Measurement

The glucose concentration was assayed by using the Beckman Glucose Analyser 2. Glucose is determined by means of the oxygen rate method employing oxygen electrode.

Before analysis samples from the enzymatic reaction were 100 times diluted.

Enzyme Preparations

Preparation 4056

The glucose oxidase/catalase preparation referred to as 4056 herein was obtained by dissolving the commercially available Maxazym® GO-P preparation, which is obtainable from Gist-brocades N.V., at the desired concentration. The catalase-Gox ratio of this preparation is 1.1 IU/SU.

Preparations L3052 and P3052

The glucose oxidase preparations rich in catalase (referred to as L3052 and P3052 herein) were obtained by fermentation of the proprietary *A.niger* strain CBS 263.94. The catalase-Gox ratios for these preparation are:

P3052 ratio catalase-Gox 140 IU/SU

L3052 ratio catalase-Gox 417 IU/SU

Enzyme preparations that are functionally identical to the "3052" preparations can be prepared by adding a commercially available *A.niger* catalase preparation, e.g. obtainable from Merck (see below), ICN (Cat. No. 190311) or from Genencor Int., to commercially obtainable glucose oxidase preparation such as the above described Maxazym® GO-P preparation.

Catalase Preparations 2 types of commercially available catalase were used:

Catalase from *A. niger* (Merck)

Catalase from Beef liver (Boehringer; Cat. No. 106.828)

Enzymatic Conversion

Unless otherwise mentioned, all the experiments were performed in laboratory fermenters (obtained from Eschweiler, Kiel), equipped with air supply system as well as a stirring device, pH control, temperature control and measurement of the dissolved oxygen concentration and the amount of oxygen in the outlet air. From this, the oxygen consumption can be calculated.

Unless otherwise mentioned, the following parameters were chosen:

temperature: 30° C.

pH: 6,0 (all solutions in 0,2M sodium phosphate buffer)

agitation: 600 rpm; when the DOC (=dissolved oxygen concentration) drops below 30%, then 900 rpm is used aeration: 6 l/min working volume: 6 l (is initial volume of glucose solution)

pH control: automatically controlled addition of a 10N NaOH solution

The conversion of glucose into gluconic acid can be followed by:

1) analysis of the glucose content;
2) analysis of the gluconic acid content;
3) the amount of sodium hydroxide added to control the pH;
4) the amount of oxygen consumption.

The advantages of methods 3 and 4 is that the information is continuously available.

In the calculation of the conversion, the dilution effect of adding the sodium hydroxide solution was taken into account.

EXAMPLE 1

To a solution of 273 g glucose per liter was added 30 000 Sarett units per liter of the glucose oxidase/catalase preparation 4056 (ratio catalase-Gox=1.1 IU/SU). Other conditions as described before.

The conversion starts immediately. The dissolved oxygen concentration is almost zero. The demand of sodium hydroxide starts immediately and is linear in the beginning. But already after about 30 minutes, the demand of sodium hydroxide and the oxygen consumption slow down, the dissolved oxygen concentration goes up and after 2 hours, the conversion has completely stopped. At that moment, less than 10% glucose is converted into gluconic acid.

EXAMPLE 2

The experiment mentioned in Example 1 was repeated with the same results. When the conversion had stopped, a considerable amount of hydrogen peroxide was detected in the broth. At this point, we added 33 000 IU catalase/l without glucose oxidase activity (obtained from Merck). An immediate hydrolysis of the hydrogen peroxide could be seen by the formation of gas bubbles and the response of the dissolved oxygen concentration probe.

The addition of catalase did not cause a restart of the conversion. From this, we conclude that the enzymatic complex was not inhibited but irreversibly inactivated by hydrogen peroxide.

We then added 30 000 SU Gox/l containing 33 000 IU catalase/l (preparation 4056). The conversion restarted immediately and the remaining glucose was completely converted into gluconic acid within 6 hours after the second addition.

EXAMPLE 3

In this experiment, 30 000 SU Gox/l containing 33 000 IU catalase/l (preparation 4056), supplemented with 33 000 IU catalase/l from Merck (ratio catalase-Gox=2.2 IU/SU) were added at the beginning of the conversion to the solution of 273 g glucose/l. Complete conversion of glucose into gluconic acid was obtained after 9 hours.

This experiment shows that a solution of 273 g glucose/l can be converted into gluconic acid in a relatively short time with glucose oxidase preparations rich in catalase.

EXAMPLE 4

We have subsequently tested enzyme preparations with higher catalase-glucose oxidase ratios. These preparation were obtained by fermentation of the *A.niger* strain CBS 263.94, however, equivalent preparation can be obtained by mixing commercially available glucose oxidase and catalase preparations in order to obtain the desired catalase-Gox ratio. These enzyme preparations used in this experiment are:

P3052 ratio catalase-Gox 140 IU/SU

L3052 ratio catalase-Gox 417 IU/SU

Table 1 summarizes the results obtained with the preparations and shows the influence of enzyme dosage and glucose concentration on the time required for complete conversion of glucose into gluconic acid.

Experiment 4,5 and 10 show that high glucose concentrations can be converted into gluconic acid. During the conversion, the dissolved oxygen concentration was almost zero. This means that it was not the amount of enzyme which was the rate limiting step but the oxygen transfer rate (OTR). The OTR in experiment 10 is rather low due to high viscosity of the concentrated glucose solution which explains the relatively long conversion time.

Experiments 6,7, 8 and 9 show that the quantity of glucose oxidase very rich in catalase can be lowered to 10 000 SU/l. The conversion time has only increased from 14 to 22 h with 360 g glucose/l. In this case, the velocity of the conversion is partly determined by the oxygen transfer rate and partly by the enzyme concentration.

TABLE 1

Enzymatic conversion of concentrated glucose solutions using glucose oxidase/catalase obtained from A. niger CBS 263.94

| Experiment | Enzyme preparation | Gox SU/l | Catalase IU/l | glucose g/l | Result: complete conversion in |
|---|---|---|---|---|---|
| 4 | P3052 | 33 360 | $4.67 \cdot 10^6$ | 273 | 9 h |
| 5 | P3052 | 33 360 | $4.67 \cdot 10^6$ | 360 | 11 h |
| 6 | L3052 | 30 000 | $1.25 \cdot 10^7$ | 360 | 14 h |
| 7 | L3052 | 20 000 | $8.34 \cdot 10^6$ | 360 | 20 h |
| 8 | L3052 | 10 000 | $4.17 \cdot 10^6$ | 360 | 22 h |
| 9 | L3052 | 40 000 | $1.67 \cdot 10^7$ | 360 | 14 h |
| 10 | P3052 | 33 360 | $4.67 \cdot 10^6$ | 545 | 33 h |

P = powder; L = liquid; Complete conversion means that the residual glucose is less than 1% of the original value or the conversion is higher than 99%.

EXAMPLE 5

Influence of Temperature

With P3052, a glucose concentration of 360 g/l, Gox activity 33 360 Su/l and catalase activity of $4.67 \times 10^6$ IU/l, temperatures of 25° C. and 40° C. were tested compared with 30° C. (experiment 5). The amount of glucose oxidase activity was analyzed at the end of the conversion.

TABLE 2

Influence of temperature on the conversion

| Experiment | Temperature ° C. | Result | Gox at the end of conversion SU/l |
|---|---|---|---|
| 5 | 30 | complete conversion in 11 h | 7 600 |
| 11 | 25 | complete conversion in 13 h | 11 800 |
| 12 | 40 | inactivation after 1 h | <3 000 |

At lower temperatures, the conversion takes a some more time but the enzyme glucose oxidase is less inactivated. At 40° C., the enzyme is inactivated almost immediately. We observe that also at 25° C. and 30° C. under the conditions mentioned, the enzyme glucose oxidase is not completely stable. In buffer solutions, glucose oxidase is perfectly stable at 25° C. and 30° C. at pH 6,0. The difference can be explained by the fact that still a low level of hydrogen peroxide is present in the reactor during the conversion despite the presence of high quantities of catalase. This can be explained by the fact that the affinity of the enzyme catalase for its substrate hydrogen peroxide is very poor (Km $H_2O_2$=1,1M).

EXAMPLE 6

Reduction of Enzyme Dosage

In this set of experiments we have determined the influence of the enzyme dosage on the time required to obtain complete conversion as well as on the residual enzyme activity, i.e. the activity left over after completion of the conversion. All parameters were as previously described, except that an initial glucose concentration of 396 g/l was used and the reactions were performed at 25° C. The other parameters were varied as indicated in Table 4. The Gox preparation used in this experiment is L3052 which is rich in catalase.

TABLE 4

Influence of enzyme dosage on conversion time and residual enzyme activity

| rpm | 900 | 900 | 900 | 900 | 600 |
|---|---|---|---|---|---|
| Gox $10^3$ SU/l | 13.0 | 6.5 | 4.33 | 3.0 | 4.33 |
| complete conversion in hours | 16 | 20 | 24 | 48 | 40 |
| residual Gox % | 61.1 | 50.4 | 29.9 | 1.2 | 13.6 |

The results show that higher initial enzyme concentrations result in shorter conversion times, but also in higher residual enzyme activities at the end of the conversion, probably caused by the shorter time of conversion. This indicates that it is possible to optimize between conversion time and enzyme costs.

Table 4 shows that also the oxygen transfer rate can be used as rate limiting factor under these conditions as a reduction of the stirring speed from 900 to 600 rpm increases the conversion time from 24 to 40 hours.

We have seen that the inactivation of the enzyme complex is less at lower temperature. This allows to (further) reduce the enzyme dosage.

At 20° C. with enzyme preparation L3052, the enzyme dosage was varied in three experiments using 360 g glucose/l. The rest of the parameters were standard.

The results are shown in Table 5.

TABLE 5

| Enzyme dosage | Time of no more addition of NaOH | Percentage of conversion |
|---|---|---|
| 4000 | 27 | 100 |
| 2500 | 43 | 100 |
| 1000 | 37 | 61 |

From this example and the other examples it can be deduced that at every temperature with a certain enzyme preparation and at every glucose concentration, the minimal amount of enzyme necessary to obtain a complete conversion can be determined. At lower temperatures this amount will be less.

From these results it can be extrapolated that the stability of the enzyme complex during conversion will be even better at lower temperatures, say 15 to 10° C.

At large scale the conversion at temperatures below 20° C. will be less interesting from a commercial point of view, because of the required cooling capacity.

EXAMPLE 7

Influence of Oxidation-Protective Agents

In this example we test several substances for their ability to protect glucose oxidase from inactivation by hydrogen peroxide. Inactivation of glucose oxidase was tested under the following conditions:

10 SU glucose oxidase/ml (*A.niger* glucose oxidase obtained from Sigma)

10 g $H_2O_2$/ml 0.05M phosphate buffer pH 6.0 at 30° C.
no catalase present
Table 6 presents the results

TABLE 6

Inactivation of glucose oxidase by hydrogen peroxide and effect of methionine, casein, and quinine thereon

| $H_2O_2$ | 0 | 10 g/l | 10 g/l | 10 g/l | 10 g/l |
|---|---|---|---|---|---|
| protective agent | 0 | 0 | methionine 200 mg/l | casein 200 mg/l | quinine 370 mg/l |
| t = 0 | 100 | 87 | 85 | 88 | 82 |
| t = 1.5 hr | 95 | 68 | 82 | 85 | 76 |
| t = 2.5 hr | 90 | 40 | 79 | 82 | 70 |

Table 6 demonstrates that each of the protective agents tested in this experiment is capable of reducing the inactivation of glucose oxidase by hydrogen peroxide.

EXAMPLE 8

Alternative Buffer Systems

In the examples described above, the glucose solutions were buffered with a 0.05M sodium phosphate buffer. However, the use of buffers may result in extra costs, e.g. the phosphate salt may have a negative effect on he recovery of the gluconic acid or gluconate.

We have therefore performed an experiment without any exogenously added buffer in a 300 l pilot plant with a 150 l glucose solution. Because we anticipated pH fluctuations caused by non-optimal mixing of the added sodium hydroxide, 25% of the enzyme solution was added at the start of the conversion, 25% three hours thereafter and the remaining 50% eight hours after the start of the conversion. The conditions were: total amount of enzyme. 4000 SU/l, 360 g glucose/l, air supply 1 volume/volume/minute (VVM), 25° C., pH 5.5, after 8 hours pH 5.8, 600 rpm, 1.5 bar overpressure.

In the beginning of the buffer-less conversion there were large fluctuations in pH as measured by the probe, without affecting the rate of the conversion. After several hours the fluctuations became smaller and disappeared almost completely after eight hours. Complete bioconversion was obtained in 25 hours.

The enzyme preparation used was obtained by fermentation of *A.niger* strain CBS 263.94 and had a catalase Gox ratio of 763.

We have also tested adding a 0.05M gluconic acid/gluconate buffer at the start of the conversion in order to reduce the pH fluctuation mentioned above.

The conditions in the lab fermenter were: 360 g glucose/l, 25° C., pH 6.0 (NaOH), air 1 VVM, glucose oxidase 5000 SU/l (enzyme preparation L3052).

This experiment was compared with one with 0.05M phosphate buffer.

In both experiments no problems in pH control were observed and no fluctuations in pH were seen after adding sodium hydroxide. Both conversion were complete after 25 hours with exactly the same amount of sodium hydroxide consumed.

We claim:

1. A process for converting glucose into gluconic acid in a yield of at least 50% which process comprises converting glucose at a concentration of at least 10% (w/v) into gluconic acid with glucose oxidase and catalase at an activity ratio in excess of 2.2 IU/SU and a temperature of at least about 10° C. wherein IU is defined as the International Catalase Unit and SU is defined as the Sarett glucose oxidase Unit.

2. A process according to claim 1 wherein at least one of the glucose oxidase and catalase enzymes is present in soluble form.

3. A process according to claim 2 wherein at least one of the glucose oxidase and catalase enzymes is a fungal enzyme.

4. A process according to claim 3 wherein the fungal enzyme is derived from an Aspergillus or a Penicillium species.

5. A process according to claim 3 wherein the enzyme is derived from a strain of *Aspergillus niger* belonging to the *Aspergillus niger* group.

6. A process according to claim 3 wherein the glucose oxidase and catalase enzyme are derived from the same fungal strain.

7. A process according to claim 1 which comprises a step wherein glucose is fed to a reaction mixture in which the conversion of glucose to gluconic acid occurs.

8. A process according to claim 1 wherein gluconic acid is used as a buffer.

9. A process according to claim 1 wherein no buffer is used.

10. A process according to claim 1 which further comprises including in said solution an oxidation-protective agent.

11. A process according to claim 10 wherein the oxidation-protective agent is selected from the group comprising proteinaceous material, casein, methionine, and quinine.

12. A process according to claim 1 in which a crude glucose solution or a soluble fraction obtainable from the crystallization of dextrose is used as source of glucose.

13. A process according to claim 12 which further comprises including in said solution enzymes capable of converting nonglucose compounds into glucose.

14. A process according to claim 1 wherein the catalase/glucose oxidase ratio is at least 55 IU/SU.

15. A process according to claim 14 wherein the catalase/glucose oxidase ratio is at least about 140 IU/SU.

16. A preparation comprising gluconic acid and/or its salts, produced by a process according to claim 1.

* * * * *